US009000197B2

(12) United States Patent
Krull et al.

(10) Patent No.: US 9,000,197 B2
(45) Date of Patent: *Apr. 7, 2015

(54) CONTINUOUS TRANSESTERIFICATION METHOD

(75) Inventors: Matthias Krull, Harxheim (DE); Roman Morschhaeuser, Mainz (DE)

(73) Assignee: Clariant Finance (BVI) Limited, Tortola (VG)

( * ) Notice: Subject to any disclaimer, the term of this patent is extended or adjusted under 35 U.S.C. 154(b) by 271 days.

This patent is subject to a terminal disclaimer.

(21) Appl. No.: 13/497,429

(22) PCT Filed: Sep. 3, 2010

(86) PCT No.: PCT/EP2010/005428
§ 371 (c)(1),
(2), (4) Date: Mar. 21, 2012

(87) PCT Pub. No.: WO2011/035853
PCT Pub. Date: Mar. 31, 2011

(65) Prior Publication Data
US 2012/0184758 A1 Jul. 19, 2012

(30) Foreign Application Priority Data
Sep. 22, 2009 (DE) .................. 10 2009 042 522

(51) Int. Cl.
*C11C 3/00* (2006.01)
*C07C 67/03* (2006.01)

(52) U.S. Cl.
CPC ................. *C11C 3/003* (2013.01); *C07C 67/03* (2013.01); *Y02E 50/13* (2013.01)

(58) Field of Classification Search
CPC .... H50B 6/6402; H05B 6/802; C07C 231/02; C07C 69/52; C07C 69/24
USPC ................. 554/124, 179, 170, 171, 172, 173; 219/678, 686, 702, 710, 745, 746, 756, 219/757
See application file for complete search history.

(56) References Cited

U.S. PATENT DOCUMENTS

| | | | |
|---|---|---|---|
| 1,972,142 A | 9/1934 | Goldstein | |
| 2,601,561 A | 6/1952 | Schertz | |
| 3,024,260 A | 3/1962 | Ernst | |
| 3,050,418 A | 8/1962 | Mendelsohn et al. | |
| 3,113,026 A | 12/1963 | Sprung | |
| 3,197,473 A | 7/1965 | Klosa | |
| 3,395,162 A | 7/1968 | Lamberti | |
| 3,585,224 A | 6/1971 | Friedrich et al. | |
| 3,652,434 A | 3/1972 | Bar-Nun et al. | |
| 3,652,671 A | 3/1972 | Barron | |
| 3,682,946 A | 8/1972 | Liechti | |
| 3,836,551 A | 9/1974 | Schroeder et al. | |
| 4,133,833 A | 1/1979 | Hull | |
| 4,165,311 A | 8/1979 | Isowa et al. | |
| 4,221,948 A | 9/1980 | Jean | |
| 4,339,648 A | 7/1982 | Jean | |
| 4,582,933 A | 4/1986 | Mertens et al. | |
| 4,675,319 A | 6/1987 | Nardi et al. | |
| 4,859,796 A | 8/1989 | Hurtel et al. | |
| 4,994,541 A | 2/1991 | Dell et al. | |
| 5,114,684 A * | 5/1992 | Walker | 422/21 |
| 5,185,466 A | 2/1993 | Kozulic et al. | |
| 5,304,766 A | 4/1994 | Baudet et al. | |
| 5,326,538 A | 7/1994 | Walker | |
| 5,387,397 A | 2/1995 | Strauss et al. | |
| 5,419,815 A | 5/1995 | Doerpinghaus et al. | |
| 5,646,318 A | 7/1997 | Dery et al. | |
| 5,646,319 A | 7/1997 | Letton et al. | |

(Continued)

FOREIGN PATENT DOCUMENTS

| | | |
|---|---|---|
| CH | 681586 | 4/1993 |
| CN | 1228910 | 9/1999 |

(Continued)

OTHER PUBLICATIONS

Lertsthapornsuk, V., et al., Microwave assisted in continuous biodiesel production from waste frying palm oil and its performance in a 100 kW diesel generator, 2008, Fuel Processing Technology 89, pp. 1330-1336.*

Mazzocchia, C., et al., Fast synthesis of biodiesel from trigycerides in presence of microwave, 2006, Advances in Microwave and Radio Frequency Processing, Report of the 8th international conference on microwave and high frequency heatting held in Bayrueth, Germany, Sep. 2001, Springer Berlin Heidelberg, Part V, pp. 370-376 (18 pages).*

Cablewski, T. et al., Development and applicatin of a continuous microwave reactor for organic synthesis, 1994, J. Org. Chem., vol. 59, No. 12, pp. 3408-3412.*

International Search Report for PCT/EP2007/008681 Mail dated Jan. 29, 2008.

Translation of International Preliminary Report on Patentability for PCT/EP2007/008681, Jan. 29, 2008.

(Continued)

*Primary Examiner* — Yate K Cutliff
(74) *Attorney, Agent, or Firm* — Tod A. Waldrop

(57) ABSTRACT

The invention relates to a continuous method for producing esters, in which at least one polyol ester of formula (I) ($R^1$—COO)$_m$R$^2$ (I), where $R^1$ represents hydrogen or an optionally substituted hydrocarbon group containing 1 to 50 carbon atoms, $R^2$ represents an optionally substituted hydrocarbon group containing 2 to 10 carbon atoms, and m represents a number from 2 to 10 and is smaller than or equal to the number of carbon atoms in $R^2$, is reacted with at least one monohydric alcohol of formula (II) $R^3$—OH (II), where $R^3$ represents an optionally substituted hydrocarbon group containing 1 to 30 C atoms, using microwave radiation in a reaction tube, the longitudinal axis of which extends in the direction of propagation of the microwaves of a single-mode microwave applicator, so as to obtain at least one ester of formula (III) $R^1$—COO—$R^3$ (III), where $R^1$ and $R^3$ have the meanings indicated above.

23 Claims, No Drawings

(56) References Cited

U.S. PATENT DOCUMENTS

| | | | |
|---|---|---|---|
| 5,710,295 A | 1/1998 | Woodbury et al. | |
| 5,830,953 A | 11/1998 | Nishikawa et al. | |
| 5,856,538 A | 1/1999 | Strecker et al. | |
| 5,866,531 A | 2/1999 | Assmann et al. | |
| 5,892,115 A | 4/1999 | Aizawa et al. | |
| 5,988,877 A | 11/1999 | Hochrad et al. | |
| 6,017,426 A | 1/2000 | Semeria et al. | |
| 6,107,498 A | 8/2000 | Maisonneuve et al. | |
| 6,120,741 A * | 9/2000 | Jacquault et al. | 422/199 |
| 6,121,471 A | 9/2000 | Scott | |
| 6,127,560 A * | 10/2000 | Stidham et al. | 554/167 |
| 6,175,037 B1 | 1/2001 | Tweedy | |
| 6,291,712 B1 | 9/2001 | Saihata et al. | |
| 6,319,187 B1 | 11/2001 | Scott | |
| 6,365,885 B1 | 4/2002 | Roy et al. | |
| 6,373,040 B2 | 4/2002 | Thomas | |
| 6,614,010 B2 | 9/2003 | Fagrell et al. | |
| 6,794,510 B2 | 9/2004 | Le Bourdonnec et al. | |
| 6,867,400 B2 * | 3/2005 | Collins et al. | 219/687 |
| 6,960,627 B2 | 11/2005 | Huth et al. | |
| 6,989,351 B2 | 1/2006 | Collins et al. | |
| 7,150,836 B2 | 12/2006 | Meikrantz | |
| 7,393,920 B2 | 7/2008 | Collins et al. | |
| 7,473,739 B2 | 1/2009 | Dairoku et al. | |
| 7,759,454 B2 | 7/2010 | Falk et al. | |
| 2003/0021793 A1 | 1/2003 | Hilgers | |
| 2005/0027120 A1 | 2/2005 | Gojon-Zorrilla | |
| 2005/0272631 A1 | 12/2005 | Miracle et al. | |
| 2005/0274065 A1 | 12/2005 | Portnoff et al. | |
| 2005/0283011 A1 | 12/2005 | Hoong et al. | |
| 2006/0057482 A1 | 3/2006 | Yuasa | |
| 2006/0228088 A1 * | 10/2006 | Charlier De Chily et al. | 385/147 |
| 2006/0252884 A1 | 11/2006 | Falk et al. | |
| 2006/0291827 A1 | 12/2006 | Suib et al. | |
| 2007/0049721 A1 | 3/2007 | Nefzger et al. | |
| 2007/0060762 A1 | 3/2007 | Kawashima et al. | |
| 2008/0009541 A1 | 1/2008 | Chambers et al. | |
| 2008/0202982 A1 | 8/2008 | Tooley | |
| 2008/0264934 A1 | 10/2008 | Moreira et al. | |
| 2010/0010244 A1 | 1/2010 | Krull et al. | |
| 2010/0032284 A1 | 2/2010 | Krull et al. | |
| 2010/0076040 A1 | 3/2010 | Krull et al. | |
| 2010/0081843 A1 | 4/2010 | Krull et al. | |
| 2010/0116642 A1 | 5/2010 | Krull et al. | |
| 2010/0173107 A1 | 7/2010 | Hahn et al. | |
| 2011/0083956 A1 | 4/2011 | Krull et al. | |
| 2011/0083957 A1 | 4/2011 | Krull et al. | |
| 2011/0089019 A1 | 4/2011 | Krull et al. | |
| 2011/0089020 A1 | 4/2011 | Krull et al. | |
| 2011/0089021 A1 | 4/2011 | Krull et al. | |
| 2011/0092722 A1 | 4/2011 | Krull et al. | |
| 2011/0137081 A1 | 6/2011 | Krull et al. | |
| 2012/0088885 A1 | 4/2012 | Krull et al. | |
| 2012/0088918 A1 | 4/2012 | Krull et al. | |
| 2012/0090983 A1 | 4/2012 | Krull et al. | |
| 2012/0095220 A1 | 4/2012 | Krull et al. | |
| 2012/0095238 A1 | 4/2012 | Krull et al. | |
| 2012/0103790 A1 | 5/2012 | Krull et al. | |
| 2012/0178951 A1 | 7/2012 | Krull et al. | |
| 2013/0274368 A1 | 10/2013 | Krull et al. | |
| 2013/0289206 A1 | 10/2013 | Krull et al. | |
| 2013/0296457 A1 | 11/2013 | Krull et al. | |
| 2013/0296458 A1 | 11/2013 | Krull et al. | |
| 2014/0200312 A1 | 7/2014 | Krull et al. | |

FOREIGN PATENT DOCUMENTS

| | | |
|---|---|---|
| CN | 1351954 | 6/2002 |
| CN | 1749279 | 3/2006 |
| CN | 1931980 | 3/2007 |
| DE | 480866 | 8/1929 |
| DE | 1139738 | 11/1962 |
| DE | 2620638 | 11/1977 |
| DE | 3209800 | 9/1983 |
| DE | 102005051637 | 5/2007 |
| DE | 102006047619 | 5/2010 |
| DE | 102009001382 | 9/2010 |
| DZ | 2009156 | 7/1970 |
| DZ | 224203 | 7/1985 |
| EP | 0134995 | 3/1985 |
| EP | 0207901 | 1/1987 |
| EP | 0226501 | 6/1987 |
| EP | 0383605 | 8/1990 |
| EP | 0437480 | 7/1991 |
| EP | 0722994 | 7/1996 |
| EP | 0377177 | 7/1997 |
| EP | 0884305 | 12/1998 |
| EP | 1256565 | 11/2002 |
| EP | 1291077 | 3/2003 |
| EP | 1435364 | 7/2004 |
| EP | 1491552 | 12/2004 |
| EP | 1712543 | 10/2006 |
| EP | 1775311 | 4/2007 |
| EP | 2079762 | 6/2007 |
| EP | 1849854 | 10/2007 |
| EP | 1884559 | 2/2008 |
| GB | 0385978 | 3/1931 |
| GB | 0414366 | 7/1934 |
| GB | 0719792 | 12/1954 |
| GB | 2094806 | 9/1982 |
| GB | 2095262 | 9/1982 |
| GB | 2361918 | 11/2001 |
| JP | 10330338 | 5/1997 |
| JP | 11508873 | 8/1999 |
| JP | 2003321427 | 11/2003 |
| JP | 2005322582 | 5/2004 |
| JP | 2006181533 | 12/2004 |
| JP | 2005060256 | 3/2005 |
| JP | 2006272055 | 3/2005 |
| JP | 2008031082 | 2/2008 |
| JP | 2009263497 | 11/2009 |
| WO | WO 90/03840 | 4/1990 |
| WO | WO 94/18243 | 8/1994 |
| WO | WO 95/06518 | 3/1995 |
| WO | WO 95/09821 | 4/1995 |
| WO | WO 96/14344 | 5/1996 |
| WO | WO 98/29461 | 7/1998 |
| WO | WO 98/29467 | 7/1998 |
| WO | WO 98/39370 | 9/1998 |
| WO | WO 03/014272 | 2/2003 |
| WO | WO 03/016359 | 2/2003 |
| WO | WO 03/041856 | 5/2003 |
| WO | WO 03/090669 | 11/2003 |
| WO | WO 2004/054707 | 7/2004 |
| WO | WO 2004/072031 | 8/2004 |
| WO | WO 2005/033062 | 4/2005 |
| WO | WO 2005/118526 | 12/2005 |
| WO | WO 2006/024167 | 3/2006 |
| WO | WO 2007/065681 | 6/2007 |
| WO | WO 2007/110384 | 10/2007 |
| WO | WO 2007/126166 | 11/2007 |
| WO | WO 2008/043492 | 4/2008 |
| WO | WO 2008/043493 | 4/2008 |
| WO | WO 2008/043494 | 4/2008 |
| WO | WO 2008/043495 | 4/2008 |
| WO | WO 2009/002880 | 12/2008 |
| WO | WO 2009/064501 | 5/2009 |
| WO | WO 2009/121490 | 10/2009 |

OTHER PUBLICATIONS

International Search Report for PCT/EP2007/008680 Mail dated Feb. 15, 2008.

Translation of International Preliminary Report on Patentability for PCT/EP2007/008680, Feb. 15, 2008.

International Search Report for PCT/EP2007/008679 Mail dated Feb. 4, 2008.

International Search Report for PCT/EP2007/008678 Mail dated Mar. 10, 2008.

Translation of International Preliminary Report on Patentability for PCT/EP2007/008678, Mar. 10, 2008.

(56) References Cited

OTHER PUBLICATIONS

International Search Report for PCT/EP2007/008677 Mail dated Mar. 3, 2008.
Translation of International Preliminary Report on Patentability for PCT/EP2007/008677, Mar. 3, 2008.
International Search Report for PCT/EP2009/001989 mail dated Jun. 10, 2009.
Translation of International Preliminary Report on Patentability for PCT/EP2009/001989, dated Oct. 14, 2010.
International Search Report for PCT/EP2009/001985 mail dated Jun. 10, 2009.
Translation of International Preliminary Report on Patentability for PCT/EP2009/001985, dated Oct. 14, 2010.
International Search Report for PCT/EP2009/001986 mail dated Jun. 18, 2009.
Translation of International Preliminary Report on Patentability for PCT/EP2009/001986, dated Oct. 14, 2010.
International Search Report for PCT/EP2009/001987 mail dated Jun. 10, 2009.
Translation of International Preliminary Report on Patentability for PCT/EP2009/001987, dated Oct. 14, 2010.
International Search Report for PCT/EP2009/001984 mail dated Jun. 10, 2009.
Translation of International Preliminary Report on Patentability for PCT/EP2009/001984, dated Oct. 14, 2010.
International Search Report for PCT/EP2009/001990 mail dated Jun. 10, 2009.
Translation of International Preliminary Report on Patentability for PCT/EP2009/001990, dated Dec. 9, 2010.
International Search Report for PCT/EP2009/001988 mail dated Jul. 9, 2009.
Translation of International Preliminary Report on Patentability for PCT/EP2009/001988, dated Jan. 27, 2011.
International Search Report for PCT/EP2010/003446 mail dated Feb. 9, 2011.
Translation of International Preliminary Report on Patentability for PCT/EP2010/003446, dated Jan. 19, 2012.
International Search Report for PCT/EP2010/003447 mail dated Feb. 9, 2011.
Translation of International Preliminary Report on Patentability for PCT/EP2010/003447, dated Feb. 09, 2012.
Written Opinion of the IPEA for PCT/EP2010/003447, dated Sep. 9, 2011.
International Search Report for PCT/EP2010/003444 mail dated Feb. 9, 2011.
Translation of International Preliminary Report on Patentability for PCT/EP2010/003444, dated Jan. 19, 2012.
Response to the Written Opinion in PCT/EP2010/003444, dated Sep. 9, 2011.
International Search Report for PCT/EP2010/003445 mail dated Sep. 1, 2010.
Translation of International Preliminary Report on Patentability for PCT/EP2010/003445, dated Jan. 5, 2012.
International Search Report for PCT/EP2010/003442 mail dated Jul. 20, 2010.
Translation of International Preliminary Report on Patentability for PCT/EP2010/003442, dated Feb. 16, 2012.
International Search Report for PCT/EP2010/003443 mail dated Feb. 9, 2011.
Translation of International Preliminary Report on Patentability for PCT/EP2010/003443, dated Feb. 16, 2012.
International Search Report for PCT/EP2010/005427 dated Mar. 21, 2011.
Translation of International Preliminary Report on Patentability for PCT/EP2010/005427, dated Mar. 21, 2011.
International Search Report for PCT/EP2010/005428 dated Jan. 27, 2011.
Translation of International Preliminary Report on Patentability for PCT/EP2010/005428, dated Jan. 27, 2011.
International Search Report for PCT/EP2011/006173 mail dated May 8, 2012.
Translation of International Preliminary Report on Patentability for PCT/EP2011/006173, dated Jul. 4, 2013.
International Search Report for PCT/EP2011/006172 mail dated Jul. 10, 2012.
Translation of International Preliminary Report on Patentability for PCT/EP2011/006172, dated Jul. 4, 2013.
International Search Report for PCT/EP2011/006175 mail dated May 9, 2012.
Translation of International Preliminary Report on Patentability for PCT/EP2011/006175, dated Jul. 4, 2013.
International Search Report for PCT/EP2011/006174 mail dated Jul. 10, 2012.
Translation of International Preliminary Report on Patentability for PCT/EP2011/006174, dated Jul. 4, 2013.
International Search Report for PCT/EP2011/006176 mail dated Aug. 1, 2012.
Translation of International Preliminary Report on Patentability for PCT/EP2011/006176, dated Jul. 4, 2013.
Fatty Acids Division, Soap Association, "Fatty Acids for Chemical Specialties: A symposium of the Soap, Detergents, and Sanitary Chemical Products Division of the Chemical Specialties Manufacturers Association," 1955, pp. 131-147.
"Microwave Synthesis" by B. L. Hayes, CEM Publishing 2002.
"Microwave vs. Conventional Heating", webpage, www.biotage.com, Jan., 2009.
"Objective Colour Assesment and Quality Control in the Chemical, Pharmaceutical and Cosmetic Industries", Application Report No. 3.9 e from Hach Lange, pp. 1-28, Feb., 2013.
(Hawley's Condensed Chemical Dictionary, 14th ed., Lewis, Richard J. Sr. ed., copyright 2002 John Wiley &.Sons, Inc., available online at http://www.knovel.comiwebiportalibrowseidisplay? EXT Knovel Display bookid=704&VerticalID=0).
A. Breccia et al, "Reaction Between Methanol and Commercial Seed Oils Under Microwave Irradiation" Internation Microwave Power Institute 1999, 34, pp. 3-8.
Advanced Organic Chemistry: Reactions, Mechanisms, and Structure; Second Edition, Jerry March, Wiley-Interscience Publication, pp. 324-331 and 382-389, 1977.
Amore et al. (Macromolecular Rapid Communications, vol. 28 (2007), Issue 4, pp. 473-477).
An et al. (J. Org. Chem. (1997), 62, 2505-2511).
Wolf, et al., AOSTRA Journal of Research 3 (1986) "Microwave Assisted Catalytic Conversion of Cyclohesxene" pp. 53-59.
Arfan et al, "Efficient Combination of Recyclable Task Specific Ionic Liquid and Microwave Dielectric.Heating for the Synthesis of Lipophilic Esters," Organic Process Research & Development vol. 9, pp. 743-748 (2005).
B. Toukoniitty, et al: "Esterification of propionic acid under microwave irradiation over an ion-exchange resin", Catalysis Today, Elsevier, NL, vol. 100, No. 3-4, Feb. 28, 2005, pp. 431-435, XP004850051.
Barbosa et al, "Niobium to alcohol mol ratio control of the concurring esterification and etherification reactions promoted by NbCl5 and A1203 catalysts under microwave irradiation," App. Catalysis A: General vol. 338, pp. 9-13 (2008).
Beilstein Substance Identification, BRN No. 6190607, 1981.
Bose et al, "Microwave promoted energy-efficient N-formylation with aqueous formic acid," Tetrahedron Let. vol. 47 (2006), pp. 4605-4607.
C. Ferroud, et al: "Microwaves-assisted solvent-free synthesis of N-acetamides by amidation or aminolysis", Tetrahedron Letters., vol. 49, Mar. 6, 2008, pp. 3004-3008, XP022602751 NL Elsevier, Amsterdam.
C. Mazzocchia et al., "Fatty acid methyl esters synthesis from triglycerides over heterogeneous catalysts in the presence of microwaves" C.R. Chimie 7 (2004) pp. 601-605.
C. Chen et al., J. Chem. Soc., Chem. Commun., 1990, 807-809.

(56) References Cited

OTHER PUBLICATIONS

Chemat, et al: "The role of selective heating in the microwave activation of heterogeneous catalysis reactions using a continuous microwave reactor", Journal of Microwave Power and Electromagnetic Energy, The Institute, Vienna, VA, US, vol. 33, No. 2, Jan. 1, 1998, pp. 88-94, XP009143773.

D. Bogdal, Microwave-assisted Organic Synthesis, Elsevier 2005.

Desai et al, "Thermal and microwave-assisted N-formylation using solid-supported reagents," Tetrahedron Let. vol. 46 (2005), pp. 955-957.

DiLuca et al, "A new, simple procedure for the synthesis of formyl amides," Synlett No. 14 (2004), pp. 2570-257.

Ella Bezdushna et al, Macromolecular Chemistry & Physics, vol. 209, pp. 1942 - 1947, XP55023715, 2008.

Ella Bezdushna et al: "Microwave-Assisted Esterification of Methacrylic Acid and Polymer-Analogous Esterification of Poly[ethylene-co-(acrylic acid)] with Dissimilar Phenols", Macromolecular Rapid Communications, vol. 208, No. 4, Feb. 19, 2007, pp. 443-448, XP55023715.

Energieeintrag im Discover, "Flexibilitaet ist Trumpf", http://www.cem.de/documents/produlde/mikro_synthese/allgemeines/flexibel.htm, Jun. 2009.

English Abstract for CH 681586, Apr. 15, 1993.
English Abstract for CN 1749279, Mar., 2006.
English Abstract for CN 1931980, Mar., 2007.
English Abstract for DD 224203, Jul. 3, 1985.
English Abstract for DE 102005051637, May 3, 2007.
English Abstract for DE 102009001382, Sep. 9, 2010.
English Abstract for DE 2620638, Nov. 24, 1977.
English Abstract for DE 480866, Aug. 1929.
English Abstract for EP 0134995, Mar. 27, 1985.
English Abstract for EP 1256565, Nov. 13, 2002.
English Abstract for JP 10330338, May, 1997.
English Abstract for JP 2003321427, Nov. 11, 2003.
English Abstract for JP 2005060256, Mar. 10, 2005.
English Abstract for JP 2005322582, May, 2005.
English Abstract for JP 2006181533, Dec., 2004.
English Abstract for JP 2006272055, Mar., 2005.
English Abstract for JP 2008031082, Feb. 14, 2008.
English Abstract for JP 52125142, Oct. 20, 1977.
English Abstract for JP 54005931, Jan. 17, 1979.
English Abstract for WO 03/090669, Nov. 6, 2003.
English Translation of CN 1351954, Jun. 5, 2002.
English translation of DIN Standard 6162, Mar., 2013.
English translation of JP 2009 263 497, 2009.

Erik Esveld, et al: "Pilot Scale Continuous Microwave Dry-Media Reactor. Part 1: Design and Modeling", Chemical Engineering and Technology, Weinheim, DE, vol. 23, No. 3, Jan. 1, 2000, pp. 279-283, XP007916923.

Erik Esveld, et al: "Pilot Scale Continuous Microwave Dry-Media Reactor Part II: Application to Waxy Esters Production", Chemical Engineering and Technology, Weinheim, DE, vol. 23, No. 5, Jan. 1, 2000, pp. 429-435, XP007916803.

Fats and Oils: Formulating and Processing for Applications, Second Ed., O'Brien, CRC Press 2003, Ch. 3, sec. 3.4.2., lines 12 - 13.

G. Pipus, et al: "Esterification of benzoic acid in microwave tubular flow reactor", Chemical Engineering Journal, Elsevier Sequoia, Lausanne, CH, vol. 76, Jan. 1, 2000, pp. 239-245, XP007916929.

Gelens et al., Tetrahedron Letters 2005, 46(21), 3751-3754.

Glasnov, et al: "Microwave-assisted synthesis under continuous-flow conditions", Macromolecular Rapid Communications, 28(4), 395-410 CODEN: MRCOE3; Jan. 1, 2007, XP002529633.

Gonzalez et al, "Tartradiamide formation by thermolysis of tartaric acid with alkylamines," Tetrahedron Letters vol. 49 2008 3925-3926.

Goretzki et al., Macromol. Rapid Commun. 2004, 25, 513-516.

H.J. Bauer, et al., Makromol. Chem., 183, 1982, pp. 2971-2976.

Iannelli et al., Tetrahedron 2005, 61, 1509-1515.

Ishihara et al, "3,4,5-Trifluorobenzeneboronic Acid as an Extremely Active Amidation Catalyst," J. Org. Chem. vol. 61, (1996), pp. 4196-4197.

J. Kremsner, et al, Top Curr Chem, (2006) 266: pp. 233-278.

J. Ruhoff, et al., J. Am. Chem. Soc., 59 (1937), 401-402.

Jain et al, "Acetylation of some organic compounds under microwave irradiation," J. Indian Chem. Soc., vol. 84, Feb. 2007, p. 188.

K. Lange, K.H. Löcherer, Taschenbuch der Hochfrequenztechnik [Pocket book of high-frequency technology], vol. 2, p. K21 ff.

Kangani, et al., "One Pot direct synthesis of amides or oxazolines from carboxylic acids using Deoxo-Fluor reagent," Tetrahedron Letters, vol. 46, (2005), pp. 8917-8920.

Karl G. Kempf et al: "A Procedure for Preparing Aryl Esters of Polyacids. The Conversion of Poly(methacrylic acid) to Poly(phenyl methacrylate)", Macromolecules, vol. 11, No. 5, Sep. 1, 1978, pp. 1038-1041, XP55024162.

Katritzky et al. (Energy & Fuels 4 (1990), 555-561).

KIC Chemicals Inc., Capric Acid, available online at http://www.kicgroup.com/capric.htm.

Konrad G. Kabza, et al: "Microwave-Induced Esterification Using Heterogeneous Acid Catalyst in a Low Dielectric Constant Medium", Journal of Organic Chemistry, American Chemical Society, Easton.; US, vol. 65, Jan. 1, 2000, pp. 1210-1214, XP007916930.

Kumar, et al., "Microwave Assisted Direct Synthesis of 2-Substituted Benzoxazoles From Carboxylic Acids Under Catalyst and Solvent-Free Conditions", Synlett, No. 9, 2005, pp. 1401-1404.

L. Perreux, et al: "Microwave effects in solvent-free esters aminolysis" Tetrahedron, Elsevier Science Publishers, Amsterdam, NL, vol. 59, No. 12, Mar. 17, 2003, pp. 2185-2189, XP004414169.

L. Perreux, et al: "Solvent-free preparation of amides from acids and primary amines under microwave irradiation", Tetrahedron, Elsevier Science Publishers, Amsterdam, NL, vol. 58, No. 11, Mar. 11, 2002, pp. 2155-2162, XP004343866.

Leadbeater, et al, Continuous-Flow Preparation of Biodiesel Using Microwave Heating:, Energy & Fuels 2007, 21, pp. 1777-1781.

M. Hajek in A. Loupe "Microwaves in Organic Synthesis", Wiley, 2006, Chapter 13, pp. 615-652.

M. S. Nery, et al., "Niobium pentachloride promoted conversion of carboxylic acds to carboxamides: Synthesis of the 4-aryl-1,2,3,4-tetraydrosoquinollne alkaloid structures"Synthesis, (2),272-276, 2003.

Machetti, et al., "Parallel Synthesis of an Amide Library Based on the 6,8-Dioxa-3-azabicyclo[3.2.1.]octane Scaffold by Direct Aminolysis of Methyl Esters," J. Comb. Chem., 2007, vol. 9, pp. 454-461.

Massicot et al., Synthesis 2001 (16), 2441-2444.

Mohan et al, "Zeolite catalyzed acylation of alcohols and amines with acetic acid under microwave irradiation," Green Chem. 2006, vol. 8, pp. 368-372.

N. Azcan et al, "Alkali catalyzed transesterification of cottonseed oil by microwave irradiation" Fuel 86 (2007) pp. 2639-2644, XP022322088.

N. Azcan et al, "Microwave assisted transesterification of rapeseed oil" Fuel 87 (2008) pp. 1781-1788, XP022611169.

N. Leadbeater et al, "Fast, Easy Preparation of Biodiesel Using Microwave Heating" Energy & Fuels 2006, 20, pp. 2281-2283.

N. Saifuddin et al, "Production of Ethyl Ester (Biodiesel) from used Frying Oil: Optimization of Transesterification Process using Microwave Irradiation" Malaysian Journal of Chemistry, 2004, vol. 6, pp. 77-82.

Noel S. Wilson, et al: "Development and Applications of a Practical Continuous Flow Microwave Cell", Organic Process Research and Development, American Chemical Society, US, vol. 8, No. 3, Jan. 1, 2004, pp. 535-538, XP007916928.

Oliver Kretschmann et al: Microwave-Assisted Synthesis of Associative Hydrogels, Macromolecular Rapid Communications, vol. 28, No. 11, Jun. 1, 2007, pp. 1265-1269, XP55023774.

Pipus et al. (First European Congress on Chemical Engineering, Firenze, Italy, May 4-7, 1997; AIDIC: Milan, Italy, 1997; pp. 45-48).

Pollington, Journal of Organic Chemistry, vol. 56, pp. 1313-1314, 1991.

Q. Yang et al. (Synth. Commun. 2008, 38, 4107-4115).

R. Jachuck, et al: "Process intensification: oxidation of benzyl alcohol using a continuous isothermal reactor under microwave irradiation", Green Chemistry, Royal Society of Chemistry, Cambridge, GB, vol. 8, Jan. 1, 2006, pp. 29-33, XP007916789.

(56) References Cited

OTHER PUBLICATIONS

R. Martinez-Palou, et al., "Synthesis of Long Chain 2-Alkyl-1-(2-hydroxyethyl)-2-imidazolines Under Microwave in Solvent-Free Conditions", Synlett 2003, No. 12, pp. 1847-1849.

R. Plantier-Royon, et al., "Synthesis of Functionalized Bis-Amides of L-(+)-Tartaric Acid and Application as Copper(II) Ligands", C.R. Chimie, 2004, pp. 119-123.

R. S. Varma, et al: "Solvent-free synthesis of amides from non-enolizable esters and amines using microwave irradiation" Tetrahedron Letters, Elsevier, Amsterdam, NL, vol. 40, No. 34, Aug. 20, 1999, pp. 6177-6180, XP004174006.

R.S. Hunter, "Conversion of Visual to Instrumental Measurements of Yellowness", 1981, JAOCS, May, pp. 606-612.

Reddy et al, "Zirconyl chloride promoted highly efficient solid phase synthesis of amide derivatives," Chinese Chemical Letters, vol. 18 (2007), pp. 1213-1217.

S. Schmitz, et al., "Access to Poly{N-[3-(dimethylamino)propyl](meth)acrylamide} via Microwave-Assisted Synthesis and Control of LCST-Behavior in Water", Macromolecular Rapid Communications, vol. 28, No. 21, Nov. 1, 2007, pp. 2080-2083.

Sebastian Sinnwell et al: "Microwave assisted hydroxyalkylamidation of poly(ethylene-co-acrylic acid) and formation of grafted poly([epsilon]-caprolactone) side chains", Journal of Polymer Science Part A: Polymer Chemistry, vol. 45, No. 16, Aug. 15, 2007, pp. 3659-3667, XP55024333.

Shore, et al, "Catalysis in Capillaries by Pd Thin Films Using Microwave-Assisted Continuous-Flow Organic Synthesis (MACOS)" Angewandte Chemie 2006, 118, pp. 2827-2832.

Synthewave 402 Manual, 2000, Prolabo, Support pages (2) and Manual pp. 1-13 (total 15 pages).

Petricci et al, "Microwave-assisted acylation of amines, alcohols, and phenols by the use of solid-supported reagents (SSRs)," J. Org. Chem. vol. 69, pp. 7880-7887, (2004).

Translation of SIPO Office Action for Application 200980101830.0, May 12, 2012.

Translation of SIPO Search Report for Application 200980101830.0, May 12, 2012.

Werner et al, "Design and synthesis of a 3,4-dehydroproline amide discovery library," J. Comb. Chem. (2007), 9(4), pp. 677-683.

Vacek et al, "Selective enzymic esterfication of fatty acids with n-butanol under microwave irradiation and under classical heating," Biotechnology Letters, vol. 22, pp. 1565-1570 (200).

Vazquez-Tato, M.P., "Microwave-Mediated Synthesis of Amides", Synlett, No. 7, 1993, p. 506.

X. Wu, et al., "Microwave Enhanced Aminocarbonylations in Water", Organic Letters, 7(15), pp. 3327-3329, 2005.

Zhaoju Yu et al: "Biodegradable polyvinyl alcohol-graftpoly(epsilon-caprolactone) comb-like polyester: Microwave synthesis and its characterization", Journal of Applied Polymer Science, vol. 104, No. 6, Jun. 15, 2007, pp. 3973-3979, XP55023817.

Zradni et al. (Synth. Commun. 2002, 32, 3525-3531).

Zradni, et al, "Minutes Synthesis of Amides from Esters and Amines Under Microwave Irradiation," Fifth International Electronic Conference on Synthetic Organic Chemistry (ECSOC-5), available at http://www.mdpi.org/ecsoc/ecsoc-5/Papers/e0013/e0013.html.

Arora et al, "A mild and efficient procedure for the conversion of aromatic carboxylic acid esters to secondary amides"Can. J. Chem, vol. 83 (2005), pp. 1137-1140.

Essen et al, "The Velocity of Propagation of Electromagnetic Waves Derived from the Resonant Frequencies of a Cylindrical Cavity Resonator," Proc. R. Soc. Lond. A (1948), vol. 194, pp. 348-361.

Katritzky et al, "Efficient microwave access to polysubstituted amidines from imidoylbenzotriazoles," J. Org. Chem, vol 71, pp. 3375-3380 (2006).

* cited by examiner

CONTINUOUS TRANSESTERIFICATION METHOD

The present invention relates to a continuous process for preparing fatty acid esters by transesterification of fatty acid esters of polyhydric alcohols under microwave irradiation on the industrial scale.

Esters of organic acids are an industrially important substance group which finds various uses, for example as a chemical raw material, for example for the production of nonionic biodegradable surfactants, or else as a renewable fuel (biodiesel). A commonly used method for preparation of esters is that of transesterification reactions, in which an ester is converted to another ester by exchange of the alcohol radical bonded to an acid group.

Particular attention has been attracted recently by processes for preparing fatty acid methyl esters from triglycerides and the use thereof as biodiesel. Concerns about preservation of the environment on the one hand, and the need for long-term, reliable and sustainable energy supply on the other hand, have caused the demand for such energy carriers to rise significantly. In addition, there is globally a regular occurrence of large amounts of waste fats, for example in (fast food) restaurants and the food and drink industry. After conversion of these used fats to biodiesel, these can be used as fuel, as a result of which the disposal costs for used fats are reduced. However, it is also possible to convert other oils and fats to biodiesel in the same way.

In the conversion of oils and fats to biodiesel, a transesterification is typically undertaken, in which the glycerol from the oils and fats consisting principally of triglycerides is exchanged for a monohydric, preferably lower alcohol such as methanol or ethanol. The transesterification is an equilibrium reaction which is generally triggered merely by mixing the reactants. However, the reaction proceeds sufficiently slowly that prolonged heating and the addition of a catalyst for acceleration of the reaction are required for commercial purposes. More recent publications are increasingly disclosing processes which work under elevated temperatures and/or pressures. The glycerol released in the transesterification is removed by phase separation, and excess alcohol is recycled after distillative removal. Finally, the resulting esters are purified, for example, by washing with water, vacuum drying and/or filtration. In the case of alkaline catalysis with alkali metal alkoxides which is typically employed, very substantial freedom from water should be ensured, since water leads to ester hydrolysis and associated soap formation with the catalyst. The triglycerides used must also have only a very low content of free fatty acids, since the soaps which otherwise form subsequently complicate the removal of glycerol, and also the further purification steps.

WO 2009/002880 discloses a process for preparing fatty acid alkyl esters under virtually critical or supercritical conditions in a pressure-resistant vessel. The reaction mixture is heated here via the wall of the vessel.

EP 1 884 559 A discloses a continuous process for transesterification of glycerides in a reaction tube at 260-420° C. under elevated pressure, preferably above 90 bar, such that methanol is present in the supercritical state, in the presence of an immobilized catalyst. Residence times in the reaction tube of at least 10 minutes are required to achieve virtually quantitative conversions.

For upscaling to a scale, of industrial interest, there are various options for processes such as that described in EP 1 884 559. Firstly, the flow rate in the reaction tube can be increased, but this requires high jacket temperatures to achieve rapid heating rates. In addition, the residence time of the reaction mixture at reaction temperature required to achieve high conversions typically also entails lengthening the reaction tube. Secondly, given a constant flow rate, the diameter of the reaction tube can be enlarged, which likewise requires an increase in the jacket temperature to ensure the necessary reaction temperature. The elevated temperatures at the tube walls lead in both cases, as a result of local overheating at these heating surfaces, often to decomposition reactions such as decarboxylation of the fatty acids, dehydration of the polyols and/or uncontrolled polymerization, especially of the unsaturated components of the triglycerides, and hence to reduced yields. Moderate jacket temperatures, in contrast, entail long residence times in the reaction tube and hence low flow rates and/or correspondingly long tubes to attain the target temperature. During such gradual heating, unwanted side reactions are likewise observed in many reactions. In all cases, the reaction volume is additionally greatly enlarged, which entails increased safety precautions in the course of performance of such a process.

A more recent approach to the transesterification of triglycerides is the microwave-supported reaction of triglycerides with lower alcohols such as methanol, with which the reaction can be accelerated.

Mazzocchia et al. (C. R. Chemie, 2004, 7, 601-605) disclose microwave-supported transesterifications of triglycerides with methanol under heterogeneous catalysis by zeolites. However, this achieves only moderate conversions at 170° C. with irradiation for two hours in a closed vessel.

Saifuddin et al. (Malaysian J. Chem. 2004, vol. 6, 77-82) disclose a process for preparing fatty acid ethyl esters by transesterification of triglycerides with ethanol. Microwave irradiation achieves a distinct acceleration of the transesterificaton compared to purely thermal conversion, but no influence on the equilibrium position was found. The reaction temperature was limited to 60° C. in order to avoid decomposition as a result of overheating.

Leadbeater et al. (Energy & Fuels, 2006, vol. 20, 2281-2283) disclose attempts to prepare fatty acid methyl esters under microwave irradiation with catalysis by KOH, wherein the batchwise transesterification of large volumes of up to 5 l is performed in a multimode microwave applicator at atmospheric pressure under reflux.

US 2005/0274065 discloses processes in which triglycerides are transesterified with alcohols in the presence of catalysts and/or under the influence of microwave energy. In one specific embodiment, the reaction mixture present in an initial charge is pumped in continuous circulation while being conducted through a stirred vessel within a microwave applicator. After repeated passage through the microwave applicator, high transesterification levels are achieved.

The scaleup of such microwave-supported transesterifications from the laboratory to an industrial scale and hence the development of plants suitable for production of several tonnes, for example several tens, several hundreds or several thousands of tonnes, per year with space-time yields of interest for industrial scale applications, however, has not been achieved to date. One cause of this is the penetration depth of microwaves into the reaction mixture, which is typically limited to a few millimeters to a few centimeters, which limits especially reactions performed in batchwise processes to small vessels or leads to very long reaction times in stirred reactors. An increase in the field strength, which is desirable for the irradiation of large amounts of substances with microwaves, is subject to tight limits, especially in the multimode systems used with preference to date for scaleup of chemical reactions, as a result of discharge processes (plasma formation) which then occur. In addition, problems with increasing the scale are presented by the inhomogeneity of the microwave field which leads to local overheating of the reaction mixture in these multimode microwave systems and is caused by more or less uncontrolled reflections of the microwaves injected into the microwave oven at the walls thereof and the reaction mixture. Moreover, the microwave absorption coefficient of the reaction mixture, which often changes during the reaction, presents difficulties with regard to a safe and reproducible reaction regime.

Breccia et al. (J. Microwave Power Elecromag. Energy 1999, 34, 3-8) disclose the continuous transesterification of vegetable oils in the presence of various catalysts under microwave irradiation. The reaction mixture is conducted here through a glass spiral mounted in a multimode microwave oven, the reaction mixture attaining the boiling temperature of the solvent in the course of a residence time in the microwave field of 2 minutes.

WO 03/014272 discloses a process for preparing fatty acid methyl esters from triglycerides and methanol under microwave irradiation, and an apparatus for continuously performing the process, in which the transesterification takes place in a stirred steel cylinder of length about 120 cm, the microwave irradiation being injected into the reaction vessel by means of a multitude of magnetrons and waveguides.

WO 90/03840 discloses a continuous process for performing various chemical reactions, for example transesterifications, in a continuous laboratory microwave reactor. However, the microwave operated in multimode does not allow upscaling to the industrial scale range. The efficiency thereof with regard to the microwave absorption of the reaction mixture is low due to the more or less homogeneous distribution of the microwave energy over the applicator space and the lack of focus of the microwave energy on the tube coil in multimode microwave applicators. A significant increase in the microwave power injected can lead to unwanted plasma discharges or to what are called thermal runaway effects. In addition, the spatial inhomogeneities of the microwave field, which vary with time and are referred to as hotspots, make it impossible to safely and reproducibly conduct the reaction on a large scale.

Leadbeater et al. (Energy & Fuels, 2007, 21, (3), pp 1777-1781) disclose the transesterification of triglycerides with methanol in a continuous stirred tank mounted in a multimode microwave applicator, with a capacity of up to 4 l under atmospheric pressure and a flow rate of up to 7.2 l/min. A comparatively low energy requirement is reported here as compared with conventionally heated transesterifications. The methyl esters thus prepared, as a result of the stirring required to prevent the enrichment of glycerol in the reaction vessel and the associated backmixing of the reaction mixture in the reaction vessel, however, still obtain comparatively large amounts of di- and triglycerides which distinctly exceed the limits fixed for biodiesel in DIN EN 14214. They accordingly cannot be marketed as biodiesel. In addition, the process is problematic in terms of safety as a result of the large reaction volume and, in addition, cannot be enlarged as desired because of the limited penetration depth of microwaves into the reaction mixture and the limited energy input in monomode microwave ovens.

Furthermore, there are known monomode or single-mode microwave applicators in which a single wave mode is employed, which spreads only in one spatial direction and is focused onto the reaction vessel by waveguides of exact dimensions. Although these instruments allow relatively high local field strengths, they have been limited to date to small reaction volumes ($\leq 50$ ml) on the laboratory scale due to the geometric requirements (for example, the intensity of the electrical field is at its greatest at its wave crests and tends toward zero at the node points).

A process for transesterification of esters was therefore sought, in which a polyol carboxylate can be reacted with a monohydric alcohol under microwave irradiation even on the industrial scale to give an ester of carboxylic acid and the monohydric alcohol. At the same time, maximum conversion rates, i.e. up to quantitative reaction rates, are to be achieved in minimum reaction times. The process should additionally enable a very energy-saving preparation of the ester from carboxylic acid and monohydric alcohol, which means that the microwave power used should be absorbed substantially quantitatively by the reaction mixture and the process should give a high energy efficiency. At the same time—aside from the polyol—only minor amounts, if any, of by-products should occur. The process should additionally enable the processing of oils and fats with an elevated proportion of free fatty acids. The esters of carboxylic acid and monohydric alcohol prepared should also have a low intrinsic color. Moreover, the process should ensure that the reaction can be conducted safely and reproducibly.

It has been found that, surprisingly, the transesterification of polyol esters can be performed in industrially relevant volumes by reaction of polyol esters with alcohols in a continuous process by only brief heating by means of irradiation with microwaves in a reaction tube whose longitudinal axis is in the direction of propagation of the microwaves from a monomode microwave applicator. At the same time, proportions of free fatty acids present in the polyol ester used are also converted to the corresponding esters, especially in the case of acidic catalysis. The microwave energy injected into the microwave applicator is absorbed virtually quantitatively by the reaction mixture. The process according to the invention additionally has high reliability in performance and gives high reproducibility of the reaction conditions established. The esters prepared by the process according to the invention exhibit a high purity and low intrinsic color which are not obtainable as compared with by conventional preparation processes without additional process steps.

The invention provides a continuous process for preparing esters, in which at least one polyol ester of the formula (I)

$$(R^1\text{—COO})_m R^2 \qquad (I)$$

in which
$R^1$ is hydrogen or an optionally substituted hydrocarbyl radical having 1 to 50 carbon atoms,
$R^2$ is an optionally substituted hydrocarbyl radical having 2 to 10 carbon atoms and
m is a number of from 2 to 10 and is less than or equal to the number of carbon atoms in $R^2$
is reacted with at least one monohydric alcohol of the formula (II)

$$R^3\text{—OH} \qquad (II)$$

in which
$R^3$ is an optionally substituted hydrocarbyl radical having 1 to 30 carbon atoms,
under microwave irradiation in a reaction tube whose longitudinal axis is in the direction of propagation of the microwaves from a monomode microwave applicator, to give at least one ester of the formula (III)

$$R^1\text{—COO—}R^3 \qquad (III)$$

in which
$R^1$ and $R^3$ are each as defined above.

Esters of the formula (I) which are preferred in accordance with the invention derive from carboxylic acids of the formula (IV)

$$R^1\text{COOH} \qquad (IV)$$

and polyols of the formula (V)

$$R^2(\text{OH})_m \qquad (V)$$

where $R^1$, $R^2$ and m are each as defined above, from which they can be prepared by known methods, for example by condensation, or are obtained in biochemical processes.

Carboxylic acids IV are generally understood here to mean compounds which have at least one carboxyl group on an optionally substituted hydrocarbyl radical having 1 to 50 carbon atoms, and formic acid. In a preferred embodiment, the hydrocarbyl radical $R^3$ is an aliphatic hydrocarbyl radical and especially an unsubstituted alkyl or alkenyl radical. In a further preferred embodiment, the hydrocarbyl radical bears one or more, for example two, three, four or more, further substituents. Suitable substituents are, for example, halogen atoms, $C_1$-$C_5$-alkoxy, for example methoxy, poly($C_1$-$C_5$-alkoxy)alkyl, keto, amide, cyano, nitrile, nitro and/or aryl groups having 5 to 20 carbon atoms, for example phenyl groups, with the proviso that these substituents are stable under the reaction conditions and do not enter into any side reactions, for example elimination reactions. The $C_5$-$C_{20}$-aryl groups may themselves in turn bear substituents, for example halogen atoms, $C_1$-$C_{20}$-alkyl, $C_2$-$C_{20}$-alkenyl, $C_1$-$C_5$-alkoxy, for example methoxy, amide, cyano, nitrile and/or nitro groups. However, the hydrocarbyl radical bears at most as many substituents as it has valences.

Particular preference is given in accordance with the invention to carboxylic esters of the formula (I) which derive from aliphatic carboxylic acids (IV) having an optionally substituted aliphatic hydrocarbyl radical $R^1$ having 2 to 40 carbon atoms and especially having 6 to 30 carbon atoms, for example having 8 to 24 carbon atoms. They may be of synthetic or preferably natural origin. The aliphatic hydrocarbyl radical may also contain heteroatoms, for example oxygen, nitrogen, phosphorus and/or sulfur, but preferably not more than one heteroatom per 2 carbon atoms and especially not more than one heteroatom per 3 carbon atoms.

The aliphatic hydrocarbyl radicals $R^1$ may be linear, branched or cyclic. They are preferably linear. If they are branched, the branch is preferably on the carbon atom adjacent to the carbonyl group or at the chain end. The ester group may be bonded to a primary, secondary or tertiary carbon atom. It is preferably bonded to a primary carbon atom. The hydrocarbyl radicals may be saturated or, if their hydrocarbyl radical $R^1$ comprises at least 2 carbon atoms, also unsaturated. Preferred unsaturated hydrocarbyl radicals preferably have one or more C=C double bonds and more preferably one, two or three C=C double bonds. Additionally preferably, they do not bear any C=C double bond conjugated to the ester group. For instance, the process according to the invention has been found to be particularly useful for transesterification of polyol esters which comprise one or more polyunsaturated carboxylic acids, since the double bonds of the unsaturated carboxylic acids are not attacked under the reaction conditions of the process according to the invention. Preferred cyclic aliphatic hydrocarbyl radicals possess at least one ring with four, five, six, seven, eight or more ring atoms.

In a particularly preferred embodiment, the polyol esters (I) derive from fatty acids. In this case, $R^1$ is an optionally substituted aliphatic hydrocarbyl radical having 6 to 50 carbon atoms. They more preferably derive from fatty acids which bear an aliphatic hydrocarbyl radical having 7 to 30 carbon atoms and especially having 8 to 26 carbon atoms, for example having 10 to 22 carbon atoms. In a preferred embodiment, the hydrocarbyl radical of the fatty acid is an unsubstituted alkyl or alkenyl radical. In a further preferred embodiment, the hydrocarbyl radical of the fatty acid bears one or more, for example two, three, four or more, further substituents.

Polyol esters (I) suitable for transesterification by the process according to the invention are esters, for example, of formic acid, acetic acid, propionic acid, butyric acid, isobutyric acid, pentanoic acid, isopentanoic acid, pivalic acid, crotonic acid, phenylacetic acid, (methoxyphenyl)acetic acid, (dimethoxyphenyl)acetic acid, 2-phenylpropionic acid, 3-phenylpropionic acid, hexanoic acid, cyclohexanoic acid, heptanoic acid, octanoic acid, nonanoic acid, neononanoic acid, decanoic acid, neodecanoic acid, undecanoic acid, neoundecanoic acid, dodecanoic acid, tridecanoic acid, tetradecanoic acid, 12-methyltridecanoic acid, pentadecanoic acid, 13-methyltetradecanoic acid, 12-methyltetradecanoic acid, hexadecanoic acid, 14-methylpentadecanoic acid, heptadecanoic acid, 15-methylhexadecanoic acid, 14-methylhexadecanoic acid, octadecanoic acid, isooctadecanoic acid, eicosanoic acid, docosanoic acid and tetracosanoic acid, myristoleic acid, palmitoleic acid, hexadecadienoic acid, delta-9-cis-heptadecenoic acid, oleic acid, petroselic acid, vaccenic acid, linoleic acid, linolenic acid, gadoleic acid, gondoic acid, eicosadienoic acid, arachidonic acid, cetoleic acid, erucic acid, docosanoic acid and tetracosenoic acid, and mixtures thereof. Additionally suitable are esters of carboxylic ester mixtures (IV) which are obtainable from natural fats and oils, for example cottonseed oil, coconut oil, peanut oil, safflower oil, corn oil, palm oil, palm kernel oil, rapeseed oil, olive oil, mustardseed oil, soybean oil, sunflower oil, and tallow oil, bone oil, fish oil and mixtures thereof.

In a preferred embodiment, the esters of the formula (I) derive from polyols of the formula (V) in which the optionally substituted hydrocarbyl radical $R^2$ is an aliphatic radical. This has preferably 2 to 8, more preferably 3 to 6 and especially 3 carbon atoms. The aliphatic radical may be linear or, if it comprises at least four carbon atoms, branched or cyclic. It may additionally be saturated or, if it has at least three carbon atoms, unsaturated. The aliphatic $R^2$ radical is preferably saturated. The hydrocarbyl radical $R^2$ may optionally bear substituents, for example $C_5$-$C_{20}$-aryl groups, and/or be interrupted by heteroatoms, for example oxygen and/or nitrogen.

Additionally preferably, the esters of the formula (I) derive from polyols of the formula (V) whose aliphatic $R^2$ radical bears two, three, four, five, six or more hydroxyl groups. The hydroxyl groups may be bonded to adjacent carbon atoms, or else to further-removed carbon atoms of the hydrocarbyl radical, but at most one OH group per carbon atom. The OH groups of the parent polyols (V) of the esters (I) may be completely or else only partially esterified. The OH groups are preferably completely or at least substantially completely esterified. "Substantially completely esterified" means that the hydroxyl number of the polyol ester (I) used is at most 50 mg KOH/g, preferably 0.1 to 30 mg KOH/g and especially 1 to 10 mg KOH/g, for example 2 to 5 mg KOH/g. The hydroxyl groups of the polyols (V) may be esterified with identical or different carboxylic acids (IV).

The process according to the invention is suitable especially for conversion of polyol esters which derive from polyols, for example ethylene glycol, 1,2-propanediol, 1,3-propanediol, neopentyl glycol, diethylene glycol, triethylene glycol, polyethylene glycol, glycerol, sorbitan, sorbitol, pentaerythritol, fructose and glucose. In a particularly preferred embodiment, the polyol (V) is glycerol.

Examples of polyol esters of the formula (I) which are particularly suitable in accordance with the invention are esters of aliphatic carboxylic acids having 6 to 30 carbon atoms and polyols having 3 to 5 carbon atoms, and especially triglycerides of fatty acids, for example triolein, tristearin and biogenic oils and fats. Equally particularly suitable for the conversion by the process according to the invention are natural fats and oils, for example cottonseed oil, coconut oil, peanut oil, safflower oil, corn oil, jatropha oil, palm kernel oil, rapeseed oil, olive oil, mustardseed oil, soybean oil, sunflower oil, and tallow oil, bone oil and fish oil.

In a preferred embodiment, the hydrocarbyl radical $R^3$ is an aliphatic radical. This aliphatic radical has preferably 1 to 24, more preferably 2 to 18 and especially 3 to 6 carbon atoms. The aliphatic radical may be linear, branched or cyclic. It may also be saturated or, if it has at least three carbon atoms, unsaturated. It is preferably saturated. The hydrocarbyl radical may bear substituents, for example halogen atoms, halogenated alkyl radicals, methoxy, $C_1$-$C_5$-alkoxyalkyl, cyano, nitrile, nitro and/or $C_5$-$C_{20}$-aryl groups, for example phenyl radicals. The $C_5$-$C_{20}$-aryl radicals may in turn optionally be substituted by halogen atoms, halogenated alkyl radicals, $C_1$-$C_{20}$-alkyl, $C_2$-$C_{20}$-alkenyl, $C_1$-$C_5$-alkoxy, for example methoxy, amide, cyano, nitrile and/or nitro groups.

In a further preferred embodiment, $R^3$ is an alkyl radical interrupted by heteroatoms. In this case, however, $R^3$ contains at most one heteroatom per two carbon atoms. Preferred heteroatoms are oxygen and nitrogen. A particularly preferred heteroatom is oxygen. When the $R^2$ radical comprises nitrogen atoms, these nitrogen atoms do not bear any acidic protons.

In a further preferred embodiment, $R^3$ is an optionally substituted $C_6$-$C_{12}$-aryl group or an optionally substituted heteroaromatic group having 5 to 12 ring members. Examples of suitable substituents are halogen atoms, halogenated alkyl radicals, and alkyl, alkenyl, alkoxy, amide, nitrile and nitro groups.

Examples of preferred aliphatic $R^3$ radicals are methyl, ethyl, n-propyl, isopropyl, n-butyl, isobutyl and tert-butyl, n-hexyl, cyclohexyl, n-octyl, isooctyl, 2-ethylhexyl, decyl, dodecyl, tridecyl, tetradecyl, hexadecyl, octadecyl and mixtures thereof. Examples of suitable alcohols of the formula II are methanol, ethanol, 2-methoxyethanol, n-propanol, isopropanol, n-butanol, isobutanol, tert-butanol, pentanol, neopentanol, n-hexanol, isohexanol, cyclohexanol, heptanol, n-octanol, isooctanol, 2-ethylhexanol, decanol, dodecanol, tridecanol, isotridecanol, tetradecanol, hexadecanol, octadecanol and mixtures thereof.

In a particularly preferred embodiment, the alcohols of the formula (II) used are unsubstituted lower aliphatic alcohols having 1 to 6 carbon atoms and especially having 1 to 3 carbon atoms, for example methanol, ethanol and propanol. Also suitable in accordance with the invention are mixtures of different alcohols (II). Especially preferred as alcohol (II) are methanol and ethanol.

The reaction of the polyol esters of the formula (I) with the alcohols (II) is effected preferably with an at least equimolar amount of the alcohol (II), based on the number of hydroxyl groups in the polyol (V). More preferably, the reaction is effected with molar ratios of alcohol (I) to hydroxyl groups in polyol (V) of 1.1:1 to 50:1, particularly of 1.5:1 to 15:1 and especially of 2:1 to 10:1, for example of 3:1 to 8:1. On completion of conversion, the excess alcohol is removed by customary separation processes, for example by distillation or flashing.

The process according to the invention is especially suitable for preparation of fatty acid methyl esters, fatty acid ethyl esters, fatty acid propyl esters and fatty acid butyl esters, for example lauric acid methyl ester, myristic acid methyl ester, palmitic acid methyl ester, margaric acid methyl ester, stearic acid methyl ester, oleic acid methyl ester, linoleic acid methyl ester, linolenic acid methyl ester, arachic acid methyl ester, behenic acid methyl ester, erucic acid methyl ester, lauric acid ethyl ester, myristic acid ethyl ester, palmitic acid ethyl ester, margaric acid ethyl ester, stearic acid ethyl ester, oleic acid ethyl ester, linoleic acid ethyl ester, linolenic acid ethyl ester, arachic acid ethyl ester, behenic acid ethyl ester, erucic acid ethyl ester, lauric acid propyl ester, myristic acid propyl ester, palmitic acid propyl ester, margaric acid propyl ester, stearic acid propyl ester, oleic acid propyl ester, linoleic acid propyl ester, linolenic acid propyl ester, arachic acid propyl ester, behenic acid propyl ester, erucic acid propyl ester, lauric acid butyl ester, myristic acid butyl ester, palmitic acid butyl ester, margaric acid butyl ester, stearic acid butyl ester, oleic acid butyl ester, linoleic acid butyl ester, linolenic acid butyl ester, arachic acid butyl ester, behenic acid butyl ester, erucic acid butyl ester, and mixtures thereof, for example coconut fatty acid methyl ester, safflower fatty acid methyl ester, palm fatty acid methyl ester, rapeseed fatty acid methyl ester, olive fatty acid methyl ester, sunflower fatty acid methyl ester, soybean fatty acid methyl ester, tallow fatty acid methyl ester, jatropha fatty acid methyl ester, coconut fatty acid ethyl ester, safflower fatty acid ethyl ester, palm fatty acid ethyl ester, rapeseed fatty acid ethyl ester, olive fatty acid ethyl ester, sunflower fatty acid ethyl ester, soybean fatty acid ethyl ester, tallow fatty acid ethyl ester, jatropha fatty acid ethyl ester, coconut fatty acid propyl ester, safflower fatty acid propyl ester, palm fatty acid propyl ester, rapeseed fatty acid propyl ester, olive fatty acid propyl ester, sunflower fatty acid propyl ester, soybean fatty acid propyl ester, tallow fatty acid propyl ester, jatropha fatty acid propyl ester, coconut fatty acid butyl ester, safflower fatty acid butyl ester, palm fatty acid butyl ester, rapeseed fatty acid butyl ester, olive fatty acid butyl ester, sunflower fatty acid butyl ester, soybean fatty acid butyl ester, tallow fatty acid butyl ester and jatropha fatty acid butyl ester.

In a preferred embodiment, the inventive transesterification reactions are accelerated or completed by working in the presence of catalysts. In this case, it is possible to use homogeneous catalysts, heterogeneous catalysts, or else mixtures thereof.

Preference is given to working in the presence of a basic catalyst or mixtures of a plurality of these catalysts. The basic catalysts used in the context of the present invention are quite generally those basic compounds which are suitable for accelerating the transesterification of carboxylic esters with alcohols. Examples of suitable catalysts are inorganic and organic bases, for example metal hydroxides, oxides, carbonates or alkoxides. In a preferred embodiment, the basic catalyst is selected from the group of the hydroxides, oxides, carbonates and alkoxides of alkali metals and alkaline earth metals. Very particular preference is given to lithium hydroxide, sodium hydroxide, potassium hydroxide, sodium methoxide, potassium methoxide, sodium carbonate, sodium tert-butoxide, potassium tert-butoxide, sodium oxide, potassium oxide and potassium carbonate. Cyanide ions are also suitable as a catalyst. These substances can be used in solid form or as a solution, for example as an alcoholic solution. Particularly preferred basic catalysts are alkali metal alkoxides, for example sodium methoxide, potassium methoxide, sodium ethoxide, potassium ethoxide, sodium tert-butoxide and potassium tert-butoxide. Particular preference is given to using the alkali metal alkoxide derived from the alcohol (II) used.

The amount of the basic catalysts used depends on the activity and stability of the catalyst under the selected reaction conditions and should be adjusted to the particular reaction. Particular preference is given to using catalytic amounts of the abovementioned reaction-accelerating compounds, preferably in the range between 0.001 and 10% by weight, more preferably in the range from 0.01 to 5% by weight, example between 0.02 and 2% by weight, based on the amount of carboxylic ester (I) and alcohol (II) used.

Preference is additionally given to working in the presence of an acidic inorganic, organometallic or organic catalyst, or mixtures of a plurality of these catalysts.

Acidic inorganic catalysts in the context of the present invention include, for example, sulfuric acid, phosphoric acid, phosphonic acid, hypophosphorous acid, aluminum sulfate hydrate, alum, acidic silica gel and acidic aluminum hydroxide. In addition, for example, aluminum compounds of the general formula $Al(OR^{15})_3$ and titanates of the general formula $Ti(OR^{15})_4$ are usable as acidic inorganic catalysts, where the $R^{15}$ radicals may each be the same or different and are each independently selected from $C_1$-$C_{10}$-alkyl radicals, for example methyl, ethyl, n-propyl, isopropyl, n-butyl, isobutyl, sec-butyl, tert-butyl, n-pentyl, isopentyl, sec-pentyl, neo-pentyl, 1,2-dimethylpropyl, isoamyl, n-hexyl, sec-hexyl, n-heptyl, n-octyl, 2-ethylhexyl, n-nonyl or n-decyl, $C_3$-$C_{12}$-cycloalkyl radicals, for example cyclopropyl, cyclobutyl, cyclopentyl, cyclohexyl, cycloheptyl, cyclooctyl, cyclononyl, cyclodecyl, cycloundecyl and cyclododecyl; preference is given to cyclopentyl, cyclohexyl and cycloheptyl. The $R^{15}$ radicals in $Al(OR^{15})_3$ or $Ti(OR^{15})_4$ are preferably each the same and are selected from isopropyl, butyl, isobutyl and 2-ethylhexyl.

Preferred acidic organometallic catalysts are, for example, selected from dialkyltin oxides $(R^{15})_2SnO$ where $R^{15}$ is as defined above. A particularly preferred representative of acidic organometallic catalysts is di-n-butyltin oxide, which is commercially available as "oxo-tin" or as Fascat® brands.

Preferred acidic organic catalysts are acidic organic compounds with, for example, phosphate groups, sulfo groups, sulfate groups or phosphonic acid groups. Particularly preferred sulfonic acids contain at least one sulfo group and at least one saturated or unsaturated, linear, branched and/or cyclic hydrocarbyl radical having 1 to 40 carbon atoms and preferably having 3 to 24 carbon atoms. Especially preferred are aliphatic sulfonic acids and aromatic sulfonic acids, especially alkylaromatic monosulfonic acids having one or more $C_1$-$C_{28}$-alkyl radicals and especially those having $C_3$-$C_{22}$-alkyl radicals. Suitable examples are methanesulfonic acid, butanesulfonic acid, benzenesulfonic acid, p-toluenesulfonic acid, xylenesulfonic acid, 2-mesitylenesulfonic acid, 4-ethylbenzenesulfonic acid, isopropylbenzenesulfonic acid, 4-butylbenzenesulfonic acid, 4-octylbenzenesulfonic acid; dodecylbenzenesulfonic acid, didodecylbenzenesulfonic acid, naphthalenesulfonic acid. It is also possible to use acidic ion exchangers as acidic organic catalysts, for example sulfo-containing poly(styrene) resins crosslinked with about 2 mol % of divinylbenzene.

Particularly preferred acidic catalysts for the performance of the process according to the invention are boric acid, phosphoric acid, polyphosphoric acid, sulfuric acid, methanesulfonic acid, alkylbenzenesulfonic acids, for example dodecylbenzenesulfonic acid and polystyrenesulfonic acids. Especially preferred are titanates of the general formula $Ti(OR^{15})_4$, and especially titanium tetrabutoxide and titanium tetraisopropoxide.

If the use of acidic inorganic, organometallic or organic catalysts is desired, in accordance with the invention, preferably 0.001 to 10% by weight, more preferably 0.01 to 5% by weight, for example between 0.02 and 2% by weight, of catalyst is used, based on the amount of carboxylic ester and alcohol used.

In a further preferred embodiment, the microwave irradiation is performed in the presence of solid catalysts. This involves suspending the solid catalyst in a reactant optionally admixed with solvent or the reaction mixture, or advantageously passing the reaction mixture optionally admixed with solvent over a fixed bed catalyst and exposing it to microwave radiation. Suitable solid catalysts are, for example, zeolites, silica gel, montmorillonite and (partly) crosslinked polystyrenesulfonic acid, which may optionally be impregnated with catalytically active metal salts.

If the transesterification is performed under temperature and pressure conditions under which the alcohol (II) used is in the supercritical state, the transesterification, in an embodiment preferred in accordance with the invention, is effected without addition of a catalyst.

The inventive transesterification is effected by mixing carboxylic ester (I) and alcohol (II), and optionally catalyst, and subsequently irradiating the reaction mixture with microwaves in a reaction tube whose longitudinal axis is in the direction of propagation of the microwaves in a monomode microwave applicator.

The reaction mixture is preferably irradiated with microwaves in a substantially microwave-transparent reaction tube within a hollow conductor connected to a microwave generator. The reaction tube is preferably aligned axially with the central axis of symmetry of the hollow conductor.

The hollow conductor which functions as the microwave applicator is preferably configured as a cavity resonator. The length of the cavity resonator is preferably such that a standing wave forms therein. Additionally preferably, the microwaves unabsorbed in the hollow conductor are reflected at the end thereof. Configuration of the microwave applicator as a resonator of the reflection type achieves a local increase in the electrical field strength at the same power supplied by the generator and increased energy exploitation.

The cavity resonator is preferably operated in $E_{01n}$ mode where n is an integer and specifies the number of field maxima of the microwave along the central axis of symmetry of the resonator. In this operation, the electrical field is directed in the direction of the central axis of symmetry of the cavity resonator. It has a maximum in the region of the central axis of symmetry and decreases to the value 0 toward the outer surface. This field configuration is rotationally symmetric about the central axis of symmetry. Use of a cavity resonator with a length where n is an integer enables the formation of a standing wave. According to the desired flow rate of the reaction mixture through the reaction tube, the temperature required and the residence time required in the resonator, the length of the resonator is selected relative to the wavelength of the microwave radiation used. n is preferably an integer from 1 to 200, more preferably from 2 to 100, particularly from 3 to 50, especially from 4 to 20, for example three, four, five, six, seven, eight, nine or ten.

The $E_{01n}$ mode of the cavity resonator is also referred to in English as the $TM_{01n}$ mode; see, for example, K. Lange, K. H. Löcherer, "Taschenbuch der Hochfrequenztechnik" [Handbook of High-Frequency Technology], volume 2, pages K21 ff.

The microwave energy can be injected into the hollow conductor which functions as the microwave applicator through holes or slots of suitable dimensions. In an embodiment particularly preferred in accordance with the invention, the reaction mixture is irradiated with microwaves in a reaction tube present in a hollow conductor with a coaxial transition of the microwaves. Microwave devices particularly preferred for this process are formed from a cavity resonator, a coupling device for injecting a microwave field into the cavity resonator and with one orifice each on two opposite end walls for passage of the reaction tube through the resonator. The microwaves are preferably injected into the cavity resonator by means of a coupling pin which projects into the cavity resonator. The coupling pin is preferably configured as a preferably metallic inner conductor tube which functions as a coupling antenna. In a particularly preferred embodiment, this coupling pin projects through one of the end orifices into the cavity resonator. The reaction tube more preferably adjoins the inner conductor tube of the coaxial transition, and is especially conducted through the cavity thereof into the cavity resonator. The reaction tube is preferably aligned axially with a central axis of symmetry of the cavity resonator. For this purpose, the cavity resonator preferably has one central orifice each on two opposite end walls for passage of the reaction tube.

The microwaves can be fed into the coupling pin or into the inner conductor tube which functions as a coupling antenna, for example, by means of a coaxial connecting line. In a preferred embodiment, the microwave field is supplied to the resonator via a hollow conductor, in which case the end of the coupling pin projecting out of the cavity resonator is conducted into the hollow conductor through an orifice in the wall of the hollow conductor, and takes microwave energy from the hollow conductor and injects it into the resonator.

In a specific embodiment, the reaction mixture is irradiated with microwaves in a microwave-transparent reaction tube which is axially symmetric within an $E_{01n}$ round hollow conductor with a coaxial transition of the microwaves. In this case, the reaction tube is conducted through the cavity of an inner conductor tube which functions as a coupling antenna into the cavity resonator. In a further preferred embodiment, the reaction mixture is irradiated with microwaves in a microwave-transparent reaction tube which is conducted through an $E_{01n}$ cavity resonator with axial introduction of the microwaves, the length of the cavity resonator being such as to form n=2 or more field maxima of the microwave. In a further preferred embodiment, the reaction mixture is irradiated with microwaves in a microwave-transparent reaction tube which is conducted through an $E_{01n}$ cavity resonator with axial introduction of the microwaves, the length of the cavity resonator being such as to form a standing wave where n=2 or more field maxima of the microwave. In a further preferred embodiment, the reaction mixture is irradiated with microwaves in a microwave-transparent reaction tube which is axially symmetric within a circular cylindrical $E_{01n}$ cavity resonator with a coaxial transition of the microwaves, the length of the cavity resonator being such as to form n=2 or more field maxima of the microwave. In a further preferred embodiment, the reaction mixture is irradiated with microwaves in a microwave-transparent reaction tube which is axially symmetric within a circular cylindrical $E_{01n}$ cavity resonator with a coaxial transition of the microwaves, the length of the cavity resonator being such as to form a standing wave where n=2 or more field maxima of the microwave.

Microwave generators, for example the magnetron, the klystron and the gyrotron, are known to those skilled in the art.

The reaction tubes used to perform the process according to the invention are preferably manufactured from substantially microwave-transparent, high-melting material. Particular preference is given to using nonmetallic reaction tubes. "Substantially microwave-transparent" is understood here to mean materials which absorb a minimum amount of microwave energy and convert it to heat. A measure employed for the ability of a substance to absorb microwave energy and convert it to heat is often the dielectric loss factor tan $\delta = \in''/\in'$. The dielectric loss factor tan $\delta$ is defined as the ratio of dielectric loss $\in''$ to dielectric constant $\in'$. Examples of tan $\delta$ values of different materials are reproduced, for example, in D. Bogdal, Microwave-assisted Organic Synthesis, Elsevier 2005. For reaction tubes suitable in accordance with the invention, materials with tan $\delta$ values measured at 2.45 GHz and 25° C. of less than 0.01, particularly less than 0.005 and especially less than 0.001 are preferred. Preferred microwave-transparent and thermally stable materials include primarily mineral-based materials, for example quartz, aluminum oxide, sapphire, zirconium oxide, silicon nitride and the like. Other suitable tube materials are thermally stable plastics, such as especially fluoropolymers, for example Teflon, and industrial plastics such as polypropylene, or polyaryl ether ketones, for example glass fiber-reinforced polyetheretherketone (PEEK). In order to withstand the temperature conditions during the reaction, minerals, such as quartz or aluminum oxide, coated with these plastics have been found to be especially suitable as reactor materials.

Reaction tubes particularly suitable for the process according to the invention have an internal diameter of one millimeter to approx. 50 cm, particularly between 2 mm and 35 cm, especially between 5 mm and 15 cm, for example between 10 mm and 7 cm. Reaction tubes are understood here to mean vessels whose ratio of length to diameter is greater than 5, preferably between 10 and 100,000, more preferably between 20 and 10,000, for example between 30 and 1000. The length of the reaction tube is understood here to mean the length of the reaction tube over which the microwave irradiation proceeds. Baffles and/or other mixing elements can be incorporated into the reaction tube.

$E_{01}$ cavity resonators particularly suitable for the process according to the invention preferably have a diameter which corresponds to at least half the wavelength of the microwave radiation used. The diameter of the cavity resonator is preferably 1.0 to 10 times, more preferably 1.1 to 5 times and especially 2.1 to 2.6 times half the wavelength of the microwave radiation used. The $E_{01}$ cavity resonator preferably has a round cross section, which is also referred to as an $E_{01}$ round hollow conductor. It more preferably has a cylindrical shape and especially a circular cylindrical shape.

The reaction tube is typically provided at the inlet with a metering pump and a manometer, and at the outlet with a pressure-retaining device and a cooling device, for example a heat exchanger. This makes possible reactions within a very wide pressure and temperature range. In a preferred embodiment, the reaction mixture, immediately after leaving the reaction tube, is cooled very rapidly to temperatures below 120° C., preferably below 100° C. and especially below 60° C. This can be accomplished, for example, by means of heat exchangers or adiabatic expansion. Typically, the reaction mixture is decompressed to atmospheric pressure, but it can also be decompressed to higher or lower pressures for subsequent process steps or in the case of use of specific apparatuses. For example, it has been found to be useful to decompress the reaction mixture to pressures well below atmospheric pressure for removal of solvent and/or unconverted reactants. Depending on the properties of the converted products and the further process steps provided, the cooling can be effected before or else after lowering the pressure, or at an intermediate pressure.

In a particularly preferred embodiment, the reaction mixture, after passing through the reaction tube, is transferred directly, i.e. without intermediate cooling, into an isothermal reaction zone, in which it is kept at reaction temperature for a certain time. Only after leaving the reaction zone is the reaction mixture optionally decompressed and cooled. The direct transfer from the reaction tube to the isothermal reaction zone is understood to mean that no active measures for supply and more particularly for removal of heat are taken between reaction tube and reaction zone. The temperature difference from leaving the reaction tube until entry into the reaction zone is preferably less than ±30° C., preferably less than ±20° C., more preferably less than ±10° C. and especially less than ±5° C. In a specific embodiment, the temperature of the reaction mixture on entry into the reaction zone corresponds to the temperature when leaving the reaction tube. This embodiment enables rapid and controlled heating of the reaction mixture to the desired reaction temperature without partial overheating and then residence at this reaction temperature for a defined period before it is cooled. It is thus possible to achieve an increased space-time yield, an increased energy efficiency and, in addition, safe and reproducible operation.

Useful isothermal reaction zones include all chemically inert vessels which enable residence of the reaction mixtures at the temperature established in the reaction tube. An isothermal reaction zone is understood to mean that the temperature of the reaction mixture in the reaction zone relative to the entrance temperature is kept constant within ±30° C., preferably within ±20° C., more preferably within ±10° C. and especially within ±5° C. Thus, the reaction mixture when leaving the reaction zone has a temperature which deviates from the temperature on entry into the reaction zone by not more than ±30° C., preferably ±20° C., more preferably ±10° C. and especially ±5° C.

In addition to continuous stirred tanks and tank cascades, especially tubes are suitable as the isothermal reaction zone. These reaction zones may consist of different materials, for example metals, ceramic, glass, quartz or plastics, with the proviso that they are mechanically stable and chemically inert under the selected temperature and pressure conditions. It has been found that thermally insulated vessels are particularly useful. The residence time of the reaction mixture in the reaction zone can be adjusted, for example, via the volume of the reaction zone. In the case of use of stirred tanks and tank cascades, it has been found to be equally useful to establish the residence time via the fill level of the tanks.

In a preferred embodiment, the reaction zone used is a tube. This may be an extension of the microwave-transparent heating tube downstream of the heating zone, or else a separate tube of the same or different material connected to the heating tube. For a given flow rate, the residence time of the reaction mixture can be determined over the length of the tube and/or the cross section thereof. The tube which functions as the reaction zone is thermally insulated in the simplest case, such that the temperature which exists on entry of the reaction mixture into the reaction zone is held within the limits given above. However, it is also possible, for example by means of a heat carrier or cooling medium, to supply energy in a controlled manner to the reaction mixture in the reaction zone, or remove it therefrom. This embodiment has been found to be useful especially for startup of the process. For example, the reaction zone may be configured as a tube coil or tube bundle which is within a heating or cooling bath or is charged with a heating or cooling medium in the form of a jacketed tube. The reaction zone may also be within a further microwave applicator in which the reaction mixture is treated once again with microwaves. In this case, it is possible to use either monomode or multimode applicators.

The residence time of the reaction mixture in the isothermal reaction zone is typically between 1 second and 10 hours, preferably between 10 seconds and 2 hours, more preferably between 20 seconds and 60 minutes, for example between 30 seconds and 30 minutes. After leaving the isothermal reaction zone, the reaction mixture is then in turn cooled very rapidly to temperatures below 120° C., preferably below 100° C. and especially below 60° C., preference again being given to the apparatuses and measures detailed above.

The preparation of the reaction mixture from ester (I), alcohol (II) and optionally catalyst and/or solvent can be performed continuously, batchwise or else in semibatchwise processes. For instance, the reaction mixture can be prepared in an upstream (semi)batchwise process, for example in a stirred vessel. In a preferred embodiment, the polyol ester (I) and alcohol (II) reactants, each independently optionally diluted with solvent, are not mixed until shortly before entry into the reaction tube. For instance, it has been found to be particularly useful, when using reactants which do not have unlimited mutual miscibility, to undertake the mixing of polyol ester (I) and alcohol (II) in a mixing zone, from which the reaction mixture is conveyed into the reaction tube. Additionally preferably, the reactants are supplied to the process according to the invention in liquid form. For this purpose, it is possible to use relatively high-melting and/or relatively high-viscosity reactants, for example in the molten state and/or admixed with solvent, for example in the form of a solution, dispersion or emulsion. A catalyst can, if used, be added to one of the reactants or else to the reactant mixture before entry into the reaction tube. Preference is given to using catalysts in liquid form, for example as a solution in one of the reactants or in a solvent which is inert under the reaction conditions. It is also possible to convert heterogeneous systems by the process according to the invention, in which case appropriate industrial apparatus for conveying the reaction mixture is required.

The reaction mixture can be fed into the reaction tube either at the end conducted through the inner conductor tube or at the opposite end.

By variation of tube cross section, length of the irradiation zone (this is understood to mean the length of the reaction tube in which the reaction mixture is exposed to microwave radiation), flow rate, geometry of the cavity resonator and the microwave power injected, the reaction conditions are preferably established such that the maximum reaction temperature is attained as rapidly as possible and the residence time at maximum temperature remains sufficiently short that as low as possible a level of side reactions or further reactions occurs. To complete the reaction, the reaction mixture can pass through the reaction tube more than once, optionally after intermediate cooling and/or removal of components, for example polyol, and/or addition of reactants, for example alcohol and/or catalyst. It is also possible, with the same result, to use cascades composed of two, three or more of the microwave applicators. In many cases, it has been found to be useful when the reaction product is cooled immediately after leaving the reaction tube, for example by jacket cooling or decompression.

The temperature rise caused by the microwave irradiation is preferably limited to a maximum of 500° C., for example, by regulating the microwave intensity or the flow rate and/or by cooling the reaction tube, for example by means of a nitrogen stream. The temperature can be measured, for example, at the surface of the reaction tube; it is preferably determined in the reaction mixture directly after it leaves the heating zone. It has been found to be particularly useful to perform the reaction at temperatures between 80 and a maximum of 400° C., particularly between 100 and 180° C. and especially between 120 and a maximum of 170° C., for example at temperatures between 130 and 160° C.

The duration of the microwave irradiation depends on various factors, for example the geometry of the reaction tube, the microwave energy injected, the reactants used and the desired degree of conversion. Typically, the microwave irradiation is undertaken over a period of less than 30 minutes, preferably between 0.01 second and 15 minutes, more preferably between 0.1 second and 10 minutes and especially between 1 second and 5 minutes, for example between 5 seconds and 2 minutes. The intensity (power) of the microwave radiation is adjusted such that the reaction mixture has the desired maximum temperature when it leaves the reaction tube. In a preferred embodiment, the reaction product, directly after the microwave irradiation has ended, is cooled as rapidly as possible to temperatures below 120° C., preferably below 100° C. and especially below 60° C. In a further preferred embodiment, the catalyst, if present, is neutralized directly after leaving the reaction tube.

The reaction is preferably performed at pressures between atmospheric pressure and 500 bar, more preferably between 1.5 bar and 150 bar, particularly between 3 bar and 100 bar and especially between 5 bar and 100 bar, for example between 10 bar and 50 bar. It has been found to be particularly useful to work under elevated pressure, which involves working above the boiling point (at standard pressure) of the reactants, products, any solvent present, and/or above the alcohol formed during the reaction. The pressure is more preferably adjusted to a sufficiently high level that the reaction mixture remains in the liquid state during the microwave irradiation and does not boil. In a specific embodiment, conditions under which the alcohol (II) exhibits supercritical behavior are employed. For example, the transesterification with methanol is performed, in a preferred embodiment, at temperatures above 240° C. and 81 bar.

To avoid side reactions and to prepare products of maximum purity, it has been found to be useful to handle reactants and products in the presence of an inert protective gas, for example nitrogen, argon or helium.

Although the alcohol (I) used can function as a solvent, it has often been found to be useful to work in the presence of further solvents in order, for example, to lower the viscosity of the reaction medium and/or to fluidize the reaction mixture if it is heterogeneous. For this purpose, it is possible in principle to use all solvents which are inert under the reaction conditions employed and do not react with the reactants or the products formed. An important factor in the selection of suitable further solvents is the polarity thereof, which determines firstly the dissolution properties and secondly the degree of interaction with microwave radiation. A particularly important factor in the selection of suitable further solvents is the dielectric loss $\in$" thereof. The dielectric loss $\in$" describes the proportion of microwave radiation which is converted to heat in the interaction of a substance with microwave radiation. The latter value has been found to be a particularly important criterion for the suitability of a solvent for the performance of the process according to the invention.

It has been found to be particularly useful to work in further solvents which exhibit minimum microwave absorption and hence make only a small contribution to the heating of the reaction system. Further solvents preferred for the process according to the invention have a dielectric loss $\in$" measured at room temperature and 2450 MHz of less than 10 and preferably less than 1, for example less than 0.5. An overview of the dielectric loss of different solvents can be found, for example, in "Microwave Synthesis" by B. L. Hayes, CEM Publishing 2002. Suitable solvents for the process according to the invention are especially those with $\in$" values less than 10, such as N-methylpyrrolidone, N,N-dimethylformamide or acetone, and especially solvents with $\in$" values less than 1. Examples of particularly preferred solvents with $\in$" values less than 1 are aromatic and/or aliphatic hydrocarbons, for example toluene, xylene, ethylbenzene, tetralin, hexane, cyclohexane, decane, pentadecane, decalin, and also commercial hydrocarbon mixtures, such as benzine fractions, kerosene, Solvent Naphtha, Shellsol® AB, Solvesso® 150, Solvesso® 200, Exxsol®, Isopar® and Shellsol® products. Solvent mixtures which have $\in$" values preferably below 10 and especially below 1 are equally preferred for the performance of the process according to the invention.

In a further preferred embodiment, the process according to the invention is performed in solvents with higher $\in$" values of, for example, 5 or higher, such as especially with $\in$" values of 10 or higher. This embodiment has been found to be useful especially in the conversion of reaction mixtures which themselves, i.e. without the presence of solvents and/or diluents, exhibit only very low microwave absorption. For instance, this embodiment has been found to be useful especially in the case of reaction mixtures which have a dielectric loss $\in$" of less than 10 and preferably less than 1. However, the accelerated heating of the reaction mixture often observed as a result of the solvent addition entails measures to comply with the maximum temperature.

When working in the presence of further solvents, the proportion thereof in the reaction mixture is preferably between 2 and 95% by weight, especially between 5 and 90% by weight and particularly between 10 and 75% by weight, for example between 30 and 60% by weight. Particular preference is given to performing the process without addition of a further solvent. Particular preference is likewise given to performing the process with an excess of the alcohol (II), which then also functions as a solvent.

In a further preferred embodiment, substances which have strong microwave absorption and are insoluble in the reaction mixture are added thereto. These lead to significant local heating of the reaction mixture and, as a result, to further-accelerated reactions. Examples of suitable heat collectors of this kind are graphite and boron carbide.

Microwaves refer to electromagnetic rays with a wavelength between about 1 cm and 1 m, and frequencies between about 300 MHz and 30 GHz. This frequency range is suitable in principle for the process according to the invention. For the process according to the invention, preference is given to using microwave radiation with the frequencies approved for industrial, scientific, medical, domestic or similar applications, for example with frequencies of 915 MHz, 2.45 GHz, 5.8 GHz or 24.12 GHz.

The microwave power to be injected into the cavity resonator for the performance of the process according to the invention is especially dependent on the target reaction temperature, but also on the geometry of the reaction tube and hence of the reaction volume, and on the flow rate of the reaction mixture through the reaction tube and the duration of the irradiation required. It is typically between 200 W and several hundred kW and especially between 500 W and 100 kW, for example between 1 kW and 70 kW. It can be generated by means of one or more microwave generators.

In a preferred embodiment, the reaction is performed in a pressure-resistant, chemically inert tube, in which case it is possible that the reactants and products and, if present, solvent can lead to a pressure buildup. After the reaction has ended, the elevated pressure can be used, by decompression, for volatilization and removal of volatile components and any solvent and/or to cool the reaction product. The polyol (V) and excess alcohol (II) formed as a by-product can, after cooling and/or decompression, be removed by customary processes, for example phase separation, distillation, stripping, flashing and/or absorption.

To achieve particularly high conversions, it has in many cases been found to be useful to expose the reaction product obtained, optionally after removal of product and/or by-product, again to microwave irradiation, in which case the ratio of the reactants used may have to be supplemented to replace consumed or deficient reactants.

Typically, esters prepared via the inventive route are obtained in a purity sufficient for further use and so no further workup and subsequent processing steps are required. For specific requirements, they can, however, be purified further by customary purifying processes, for example distillation, recrystallization, filtration or chromatographic processes.

The advantages of the process according to the invention lie in very homogeneous irradiation of the reaction mixture in the center of a symmetric microwave field within a reaction tube, the longitudinal axis of which is in the direction of propagation of the microwaves of a monomode microwave applicator and especially within an $E_{01}$ cavity resonator, for example with a coaxial transition of the microwaves. The inventive reactor design allows the performance of reactions also at very high pressures and/or temperatures. By increasing the temperature and/or pressure, a significant rise in the degree of conversion and yield is observed even compared to known microwave reactors, without this resulting in undesired side reactions and/or discoloration. Surprisingly, a very high efficiency is achieved in the exploitation of the microwave energy injected into the cavity resonator, which is typically above 50%, often above 80%, in some cases above 90% and in special cases above 95%, for example above 98%, of the microwave power injected, and thus gives economic and environmental advantages over conventional preparation processes, and also over prior art microwave processes.

The process according to the invention additionally allows a controlled, reliable and reproducible reaction regime. Since the reaction mixture in the reaction tube is moved parallel to the direction of propagation of the microwaves, known overheating phenomena resulting from uncontrollable field distributions, which can lead to local overheating as a result of changing intensities of the microwave field, for example in wave crests and node points, are balanced out by the flowing motion of the reaction mixture. In addition, an increase in the length and/or diameter of the reaction tube, and the selection of the wavelength of the microwave radiation, whose penetration depth into the reaction mixture increases with decreasing frequency, can increase the energy which can be transferred to the reaction mixture, and hence the throughput. The advantages mentioned thus also allow working with high microwave powers of, for example, more than 10 kW or more than 100 kW, and hence, in combination with only a short residence time in the cavity resonator, accomplishment of large production volumes of 100 or more tonnes per year in one plant.

It was surprising that, in spite of the only very short residence time of the reaction mixture in the microwave field in the flow tube with continuous flow, very substantial transesterification with conversions generally of more than 80%, often even more than 90% and especially more than 95%, for example more than 98%, based on the component used in deficiency, takes place without formation of significant amounts of by-products. In case of a corresponding conversion of these reaction mixtures in a flow tube of the same dimensions with thermal jacket heating, extremely high wall temperatures are required to achieve suitable reaction temperatures, which lead to the formation of colored species, but bring about only slight transesterification within the same time interval.

The process according to the invention thus allows very rapid, energy-saving and inexpensive preparation of carboxylic esters in high yields and with high purity in industrial scale amounts. At the same time, it is also possible to use polyol esters with an elevated content of free fatty acids. In this process—aside from the polyol (V)—no significant amounts of by-products are obtained. Such rapid and selective conversions are unachievable by conventional methods and were not to be expected solely through heating to high temperatures.

EXAMPLES

The irradiations of the reaction mixtures with microwaves were effected in an apparatus which contained, as a reaction tube, a ceramic tube (60×1 cm) which was present in axial symmetry in a cylindrical cavity resonator (60×10 cm) (irradiation zone). At one of the ends of the cavity resonator, this ceramic tube ran through the cavity of an inner conductor tube which functions as a coupling antenna. The microwave field with a frequency of 2.45 GHz, generated by a magnetron, was injected into the cavity resonator by means of the coupling antenna ($E_{01}$ cavity applicator; monomode), in which a standing wave formed. In the case of use of an isothermal reaction zone, the heated reaction mixtures, immediately after leaving the reaction tube, were conveyed through a thermally insulated stainless steel tube (3.0 m×1 cm, unless stated otherwise). After leaving the reaction tube, or in the case of use of the isothermal reaction zone after leaving said zone, the reaction mixtures were decompressed to atmospheric pressure and cooled immediately to the temperature specified by means of an intensive heat exchanger, and the catalyst was neutralized.

The microwave power was adjusted over the experimental duration in each case in such a way that the desired temperature of the reaction mixture at the end of the reaction tube was kept constant. The microwave powers specified in the experimental descriptions therefore represent the mean value of the incident microwave power over time. The measurement of the temperature of the reaction mixture was undertaken by means of a Pt100 temperature sensor immediately after departure from the reaction tube (distance about 15 cm in an insulated stainless steel capillary, Ø 1 cm) and, if appropriate, after departure from the reaction zone. Microwave energy not absorbed directly by the reaction mixture was reflected at the opposite end of the cavity resonator from the coupling antenna; the microwave energy which was also not absorbed by the reaction mixture on the return path and reflected back in the direction of the magnetron was passed with the aid of a prism system (circulator) into a water-containing vessel. The difference between energy injected and power loss (determined by the heating of the water load) was used to calculate the microwave energy introduced into the reaction mixture.

By means of a high-pressure pump and of a suitable pressure-release valve, the reaction mixture in the apparatus was placed under such a working pressure that was sufficient always to keep all reactants and products or condensation products in the liquid state. The reaction mixtures were pumped through the apparatus at a constant flow rate and the residence time in the reaction tube (irradiation zone) and reaction zone was adjusted by modifying the flow rate.

The products were analyzed by means of $^1$H NMR spectroscopy at 500 MHz in $CDCl_3$.

Example 1

Preparation of Coconut Fatty Acid Methyl Ester

A 10l Büchi stirred autoclave with gas inlet tube, stirrer, internal thermometer and pressure equalizer was initially charged with 3.43 kg of coconut fat (5 mol/molecular weight 686 g/mol) which were heated to 55° C. At this temperature, 1.23 kg of methanol (40 mol) and 50 g of sodium methoxide as a catalyst were added gradually and the mixture was homogenized by stirring.

The reaction mixture thus obtained was pumped continuously through the apparatus at 5 l/h at a working pressure of 30 bar and exposed to a microwave power of 2.0 kW, 90% of which was absorbed by the reaction mixture. The residence time of the reaction mixture in the reaction tube was approx. 34 seconds. At the end of the reaction tube, the reaction mixture had a temperature of 220° C. Directly after leaving the reaction tube, the reaction mixture was cooled to 50° C. and neutralized with acetic acid.

The reaction product was pale yellowish in color. After removal of glycerol formed and excess methanol, 3.4 kg of coconut fatty acid methyl ester were obtained with a purity of 98%. The contents of mono- and diglycerides were 1.2% and 0.2% by weight respectively.

Example 2

Preparation of Rapeseed Fatty Acid Methyl Ester

A 10l Büchi stirred autoclave with gas inlet tube, stirrer, internal thermometer and pressure equalizer was initially charged with 4.39 kg of rapeseed oil (5 mol/molecular weight 878 g/mol) which were heated to 55° C. At this temperature, 1.12 kg of methanol (35 mol) and 50 g of sodium methoxide as a catalyst were added gradually and the mixture was homogenized by stirring.

The reaction mixture thus obtained was pumped continuously through the apparatus at 4.5 l/h at a working pressure of 35 bar and exposed to a microwave power of 1.95 kW, 92% of which was absorbed by the reaction mixture. The residence time of the reaction mixture in the irradiation zone was approx. 38 seconds. On departure from the reaction tube, the reaction mixture had a temperature of 205° C. and was transferred directly into the isothermal reaction zone at this temperature. At the end of the reaction zone, the reaction mixture had a temperature of 195° C. Directly after leaving the reaction zone, the reaction mixture was cooled to room temperature and neutralized with lactic acid.

The reaction product was pale yellowish in color. After removal of glycerol formed and excess methanol, 4.4 kg of rapeseed fatty acid methyl ester were obtained with a purity of >99%. The product contained 0.6% by weight of monoglycerides and <0.2% by weight of diglycerides (detection limit).

Example 3

Preparation of Rapeseed Fatty Acid Ethyl Ester

A 10l Büchi stirred autoclave with gas inlet tube, stirrer, internal thermometer and pressure equalizer was initially charged with 6.45 kg of rapeseed oil (7 mol/molecular weight 878 g/mol) which were heated to 55° C. At this temperature, 2.58 kg of ethanol (56 mol) and 50 g of sodium ethoxide as a catalyst were added gradually and the mixture was homogenized by stirring.

The reaction mixture thus obtained was pumped continuously through the apparatus at 5 l/h at a working pressure of 35 bar and exposed to a microwave power of 2.2 kW, 90% of which was absorbed by the reaction mixture. The residence time of the reaction mixture in the irradiation zone was approx. 34 seconds. On departure from the reaction tube, the reaction mixture had a temperature of 207° C. and was transferred directly into the isothermal reaction zone at this temperature. At the end of the reaction zone, the reaction mixture had a temperature of 198° C. Directly after leaving the reaction zone, the reaction mixture was cooled to room temperature and neutralized with lactic acid.

The reaction product was yellowish in color. After removal of glycerol formed and excess ethanol, 6.47 kg of rapeseed fatty acid ethyl ester were obtained with a purity of 96%. The product contained 2.2% by weight of monoglycerides and 0.5% by weight of diglycerides.

Example 4

Preparation of Rapeseed Fatty Acid Methyl Ester from Rapeseed Oil with Elevated Content of Free Fatty Acids A 10l Büchi stirred autoclave with gas inlet tube, stirrer, internal thermometer and pressure equalizer was initially charged with 4.62 kg of rapeseed oil (5 mol/molecular weight 878 g/mol) with a proportion of 5% by weight of free rapeseed oil fatty acid (280 g/mol), which had a total acid number of the oil of 10 mg KOH/g, which were heated to 55° C. At this temperature, 1.12 kg of methanol (35 mol) and 50 g of methanesulfonic acid as a catalyst were added gradually and the mixture was homogenized by stirring.

The reaction mixture thus obtained was pumped continuously through the apparatus at 5 l/h at a working pressure of 35 bar and exposed to a microwave power of 2.1 kW, 92% of which was absorbed by the reaction mixture. The residence time of the reaction mixture in the irradiation zone was approx. 34 seconds. At the end of the reaction tube, the reaction mixture had a temperature of 199° C. Directly after leaving the reaction tube, the reaction mixture was cooled to room temperature.

The reaction product was pale yellowish in color. After removal of glycerol formed and excess methanol, washing with dilute aqueous sodium hydrogen carbonate solution freed the reaction product of catalyst residues. The phase separation proceeded without any problem, which demonstrates the absence of fatty acid salts, which are strong emulsifiers. The upper organic phase removed had a residue acid number of 0.9 mg KOH/g. The rapeseed fatty acid methyl ester thus prepared contained 0.7% by weight of monoglycerides and 0.2% by weight of diglycerides.

The invention claimed is:

1. A continuous process for preparing esters, comprising the steps of providing a substantially microwave-transparent reaction tube, wherein the substantially microwave-transparent reaction tube has a longitudinal axis and wherein the longitudinal axis is parallel in direction to propagation of microwaves from a monomode microwave applicator, continuously feeding and mixing at least one polyol ester of the formula (I)

$(R^1-COO)_m R^2$      (I), in which
$R^1$ is hydrogen or an optionally substituted hydrocarbyl radical having 1 to 50 carbon atoms,
$R^2$ is an optionally substituted hydrocarbyl radical having 2 to 10 carbon atoms and
m is a number of from 2 to 10 and is less than or equal to the number of carbon atoms in $R^2$
with at least one monohydric alcohol of the formula (II)

$R^3-OH$      (II)

in which
$R^3$ is an optionally substituted hydrocarbyl radical having 1 to 30 carbon atoms, to form a reaction mixture, continuously reacting the reaction mixture under microwave irradiation in the substantially microwave-transparent reaction tube to give at least one ester of the formula (III)

$R^1-COO-R^{3\,m}$      (III)

in which

R¹ and R³ are each as defined above.

2. The process as claimed in claim 1, in which the reaction mixture is irradiated with microwaves in the substantially microwave-transparent reaction tube within a hollow conductor connected via waveguides to a microwave generator.

3. The process as claimed in claim 1, in which the microwave applicator is configured as a cavity resonator.

4. The process as claimed in claim 1, in which the microwave applicator is configured as a cavity resonator of the reflection type.

5. The process as claimed in claim 2, in which the reaction tube is aligned axially with a central axis of symmetry of the hollow conductor.

6. The process as claimed in claim 1, in which the reaction mixture is irradiated in a cavity resonator with a coaxial transition of the microwaves.

7. The process as claimed in claim 3, in which the cavity resonator is operated in $E_{01n}$ mode where n is an integer from 1 to 200.

8. The process as claimed in claim 3, in which a standing wave forms in the cavity resonator.

9. The process as claimed in claim 1, in which the reaction mixture is heated by the microwave irradiation to temperatures between 80 and 500° C.

10. The process as claimed in claim 1, in which microwave power of the monomode microwave applicator can be regulated and wherein incident microwave power is regulated via the difference between target and actually attained maximum temperature of the reaction mixture.

11. The process as claimed in claim 1, in which the microwave irradiation is effected at pressures above atmospheric pressure to form a pressurized reaction mixture.

12. The process as claimed in claim 11, in which the pressurized reaction mixture heated to reaction temperature by means of microwaves, after leaving the reaction tube, is transferred directly into an isothermal reaction zone adjoining the reaction tube and, after leaving the isothermal reaction zone, is cooled.

13. The process as claimed in claim 1, in which $R^1$ is an optionally substituted aliphatic hydrocarbyl radical having 2 to 40 carbon atoms.

14. The process as claimed in claim 1, in which $R^1$ is an alkyl or alkenyl radical.

15. The process as claimed in claim 1, in which $R^1$ is an aliphatic hydrocarbyl radical having 7 to 30 carbon atoms.

16. The process as claimed in claim 1, in which $R^2$ is an optionally substituted aliphatic hydrocarbyl radical.

17. The process as claimed in claim 1, in which the polyol ester (I) is selected from the group consisting of esters of ethylene glycol, 1,2-propanediol, 1,3-propanediol, neopentyl glycol, diethylene glycol, triethylene glycol, polyethylene glycol, glycerol, sorbitan, sorbitol, pentaerythritol, fructose and glucose.

18. The process as claimed in claim 1, in which $R^3$ is an aliphatic radical having 1 to 24 carbon atoms.

19. The process as claimed in claim 1, in which the alcohol of the formula (II) is selected from the group consisting of methanol and ethanol.

20. The process as claimed in claim 1, in which $R^3$ is an alkyl radical interrupted by heteroatoms.

21. The process as claimed in claim 1, in which $R^3$ is an optionally substituted $C_6$-$C_{12}$-aryl group or an optionally substituted heteroaromatic group having 5 to 12 ring members.

22. The process as claimed in claim 1, in which 0.001 to 10% by weight, based on the weight of carboxylic ester (I) and alcohol (II), of a basic catalyst is used.

23. The process as claimed in claim 1, in which 0.001 to 10% by weight, based on the weight of carboxylic ester (I) and alcohol (II), of an acidic catalyst is used.

\* \* \* \* \*